United States Patent
Norman et al.

(10) Patent No.: US 7,220,409 B2
(45) Date of Patent: May 22, 2007

(54) STABILIZATION OF IMMUNOGLOBULINS AT LOW PH

(75) Inventors: Daniel Norman, Lund (SE);
Marie-Louise Johansson, Bjärred (SE);
Björn Åkesson, Lund (SE); Lena Nyberg, Lund (SE); Marie Paulsson, Lund (SE)

(73) Assignee: Probi AB, Lund (SE)

( * ) Notice: Subject to any disclaimer, the term of this patent is extended or adjusted under 35 U.S.C. 154(b) by 172 days.

(21) Appl. No.: 10/362,358

(22) PCT Filed: Aug. 29, 2001

(86) PCT No.: PCT/SE01/01836

§ 371 (c)(1),
(2), (4) Date: Jul. 15, 2003

(87) PCT Pub. No.: WO02/18442

PCT Pub. Date: Mar. 7, 2002

(65) Prior Publication Data

US 2004/0028667 A1    Feb. 12, 2004

(30) Foreign Application Priority Data

Aug. 29, 2000 (SE) .................................. 0003045

(51) Int. Cl.
*A61K 39/395* (2006.01)
*A61K 31/715* (2006.01)
*A61K 35/78* (2006.01)

(52) U.S. Cl. ................ 424/93.45; 424/439; 424/130.1; 424/750; 514/54

(58) Field of Classification Search ............... 424/93.4, 424/93.45, 130.1, 143.1, 145.1, 147.1–150, 424/157.1–161, 439, 750; 426/549, 590; 514/54
See application file for complete search history.

(56) References Cited

U.S. PATENT DOCUMENTS

| | | | | |
|---|---|---|---|---|
| 3,640,729 A | * | 2/1972 | Ronai et al. ................. | 426/620 |
| 4,402,938 A | * | 9/1983 | Collins et al. ............... | 424/535 |
| 4,477,432 A | * | 10/1984 | Hardie ....................... | 424/165.1 |
| 5,017,372 A | * | 5/1991 | Hastings ..................... | 424/157.1 |
| 5,143,848 A | * | 9/1992 | Scholten et al. ............... | 436/8 |
| 5,147,548 A | * | 9/1992 | Hies et al. ................... | 210/639 |
| 5,190,755 A | * | 3/1993 | Molin et al. ................. | 424/93.45 |

(Continued)

FOREIGN PATENT DOCUMENTS

SE                448062            1/1987

(Continued)

OTHER PUBLICATIONS

Chen et al., Effect of Thermal Protectants on Bovine Milk IgG, 1998, J Agric. Food Chem., 46, 3570-3576.*

*Primary Examiner*—Sharon E. Kennedy
(74) *Attorney, Agent, or Firm*—Oblon, Spivak, McClelland, Maier & Neustadt, P.C.

(57) ABSTRACT

The present invention provides a method of stabilizing immunoglobulins in a solution having a pH below 4 by adding cereals or hydrolysed cereal products in an amount sufficient to prevent degradation. The present invention also provides a health drink or sports drink comprising immunoglobulins in a solution having a pH of 2.7–3.8 containing cereals or hydrolysed cereal products in an amount sufficient to prevent degradation of the immunoglobulins.

19 Claims, 5 Drawing Sheets

U.S. PATENT DOCUMENTS

| | | | |
|---|---|---|---|
| 5,342,641 A * | 8/1994 | Masutake et al. ........... 426/549 |
| 5,531,989 A * | 7/1996 | Paul ......................... 424/93.4 |
| 6,096,870 A | 8/2000 | Mozaffar et al. |

FOREIGN PATENT DOCUMENTS

| WO | 8908405 | 9/1989 |
|---|---|---|
| WO | 9613271 | 5/1996 |
| WO | 9716977 | 5/1997 |
| WO | 0047063 | 8/2000 |

\* cited by examiner

STABILIZATION OF IMMUNOGLOBULINS AT LOW PH

The present invention refers to a method of stabilising immunoglobulins, especially IgG, in a solution having a low pH, and to a health drink or sports drink having a content thereof.

BACKGROUND OF THE INVENTION

Immunoglobulins, or antibodies, are a group of glycoproteins present in serum and tissue fluids of all mammals. There are five isotypes of Igs which all have a similar basic structure. The basic structure is a unit consisting of two identical light polypeptide chains and two indentical heavy polypeptide chains linked together by disulfide bonds. IgG is the major immunoglobulin in normal human serum accounting for 70–75% of the total immunoglobulin pool. The IgG class is the major antibody of secondary immune responses and the exclusive antitoxin class. Antibodies contribute to the protection against bacterial infections by agglutination and stimulation of phagocytosis.

Bovine colostrum, which can be defined as milk from the first three milkings or milk collected during the first 24 hours after parturition, is rich in nutrients, antibodies and growth factors. According to another, more common definition colostrum is obtained during the first three days after calving. It contains three classes of immunoglobulins, IgG, commonly divided into two subclasses IgG1 and IgG2, IgA and IgM. The main natural function of the colostrum immunoglobulins is to provide the newborn calf with passive immunity. The quality of colostrum is referred to its concentration of immunoglobulins; a good quality colostrum has >60 mg immunoglobulins/ml corresponding to >30 mg IgG1/ml.

Dietary exposure to bovine IgG can have several effects on the human immune system. As any foreign protein bovine IgG may represent a potent antigen and stimulate production of antibodies. Both bovine IgG subclasses bind to human monocytes, but only bovine IgG1 bind to human B cells. This binding to human mononuclear cells may influence the human mucosal and systemic immune responses. IgG1 of bovine origine has been shown to protect against infection by various enteric pathogens in animal and in humans.

There are many commercial products based on colostrum on the market, most of which are used as in the form of powder or tablets, beverages or food as nutritional food supplements or immune stimulants for health-oriented consumers and sports enthusiasts. Bovine colostrum supplementation in addition increases serum concentrations of growth factors and enables athletes to train harder, longer and more frequently.

PRIOR ART

The stability of immunoglobulins is of great importance when formulating a product. The stability of bovine IgG in milk products depends on the severity of the thermal treatment used in the various commercial processes.

The pH is important for the stability of immunoglobulins. Bovine IgG has been shown to be stable at neutral pH but with decreasing pH the stability is deteriorated. At pH 3, for instance, the content of IgG has been reduced by 73% after 2 hours. (Chao-Cheng Chen et al., Effect of Thermal Protectants on the Stability of Bovine Milk Immunoglobulin G, J. Agric. Food Chem. 1998, 46, 3570–3576.)

The stability of IgG against acid and alkali was increased by encapsulation of IgG in a water in oil in water multi-emulsion (Chao-Cheng Chen et al., Efficiency and Protective Effect of Encapsulation of Milk Immunoglobulin G in Multiple Emulsion, J. Agri. Food Chem. 1999, 47, 407–410). The IgG loss during the preparation of the multiple emulsion was, however, almost 41–50% and the stability of the emulsion decreased as time went on.

WO 95/101 92 relates to a nutritional drink based on colostrum which comprises a colostrum fraction obtained by defatting and precipitating the casein and/or ultrafiltrating the defatted colostrum. The drink obtained most probably had a pH above 5.

PCT/SE00/01024 refers to a sports drink containing viable lactobacilli and conventional additives. The sports drink can also contain proteins, such as whey proteins supplying essential amino acids. It is mentioned that bovine colostrum could be a possible source of proteins, but not as a source of immuno-globulins.

U.S. Pat. No. 4,477,432 discloses an oral pharmaceutical composition comprising human immune globulin in a pharmaceutically acceptable carrier. The composition, which has a pH of about 4–8, preferably 6–7, also contains a carbohydrate in an amount of 1–20% by weight as a stabilising agent.

DESCRIPTION OF THE INVENTION

The present inventin refers to a method of stabilising immunoglobulins in a solution having a pH below 4, which is characterized in that cereals or hydrolysed cereal products are added in an amount sufficient to prevent degradation. As examples of cereals can be mentioned oats, rye, wheat and barley. Hydrolysed cereal products comprise enzymatically treated cereals, which treatment brings about a degradation of different components thereof. As an example of a hydrolysed cereal product can be mentioned oatmeal soup, which is obtained by adding malted barley flour to oat flour and water, and heating.

The immunoglobulins are preferably selected from the group consisting of IgG, IgA, IgM and IgY. Sources of immuno-globulins are for instance bovine colostrum containing IgGs and egg containing IgY. Also antibodies against different antigens, such as intestinal bacteria, can be a possible source. According to a preferred aspect of the invention the immunoglobulins are bovine IgGs.

In order to prevent degradation of the immunoglobulins, oatmeal soup could be added to the solution in an amount of from 2% up to 100% by weight of the solution, that is about 2–99%. Oatmeal soup in this context refers to a product obtained after heating a mixture of oat flour, water, and enzymes for degrading the starch.

If oat flour is added, the preferred amount could be 0.3–15% by weight of the solution.

According to another aspect of the invention lipids from oats are added in an amount of 0.03–1.5% by weight of the solution.

The invention also refers to a method of stabilising immunoglobulins in a solution having a low pH, which is characterised in that in addition to cereals or hydrolysed cereal products mono-, di- and/or oligosaccharides are added in an amount sufficient to prevent degradation. As examples of said sugars can be mentioned fructose, glucose, sucrose, maltose, lactose, inulin, and dextrins.

According to a preferred aspect the invention refers to a method of stabilising, wherein a combination of cereals, sugars and fruit concentrate is added to the solution.

The invention especially refers to a health drink or sports drink comprising immunoglobulins in a solution having a pH of 2.7–3.8, preferably 3.1–3.4, which is characterized in containing cereals or hydrolysed cereal products in an amount sufficient to prevent degradation of the immunoglobulins. A pH within this interval is generally obtained in a beverage containing optionally fermented cereals or hydrolysed cereal products in combination with for instance a fruit juice.

According to a preferred aspect the immunoglobulins are bovine IgGs.

A preferred drink contains an IgG concentrate in an amount of 0.5–50 mg IgG/ml, preferably 3–20 mg/ml. A drink according to the present invention preferably contains an IgG concentrate derived from bovine colostrum.

The health drink or sports drink of the invention also can comprise a probiotic bacterium, such as a strain of *Lactobacillus* having the ability to bind to the intestinal mucosa, or a strain giving rise to increased amounts of propionic acid or acetic acid in colon, or a strain having the ability to increase the production of mucin in colon. Examples of strains are strains of *Lactobacillus plantarum* belonging to a cluster having a restriction endonuclease analysis similarity of more than 55% to the strain *Lactobacillus plantarum* 299, deposition number bSM 6595, which strains have been described in the International Patent Application WO 96/29083. A preferred strain is *Lactobacillus plantarum* 299v, DSM 9843. The concentration of the probiotic bacterium in the drink should be at least $1\times10^6$ cfu/ml, preferably $5\times10^7$–$2\times10^9$ cfu/ml, but also higher or lower amounts can be used whenever applicable.

A drink according to the invention preferably comprises sugars, fruit concentrate and fermented oatmeal soup.

Colostrum is naturally rich in IgG and administration of bovine colostrum IgG is believed to have several positive effects on the human immune system. Oral administration of different probiotic strains of lactobacilli also has been shown to have positive immunomodulatory effects, and consequently a composition, such as a health drink or sports drink, combining IgG and probiotic lactobacilli may be of particular interest for obtaining a positive immunomodulatory effect in humans.

It can be speculated in the mechanisms behind the stabilisation of the immunoglobulins at low pH according to the invention. Destabilising of immunoglobulins can be caused by a change in the redox potential leading to an opening of the disulfide briges of the proteins. In cereals there are redox systems which protect the disulfide bridges of proteins from being reduced to —SH groups. The redox processes of oats are connected into a complex pattern, which is today only partially known. Another possible way of action is by means of surfactant molecules, such as polar lipids, which bind to hydrophobic regions of the protein. A drop of the pH to a value below the isoelectrical point in general brings about a denaturation of the protein, mainly by repulsion by those groups which become negatively loaded. Such a denaturation can be compensated for by surfactant molecules binding to hydrophobic regions on the protein which are exposed towards the water. Oats contain about 9–10% by weight of lipids, and more than 10% of said lipids are polar lipids, that is phospholipids and galactolipids.

EXPERIMENTALS

Materials and Methods

In the following experiments two different IgG products derived from bovine colostrum were used. The different products were prepared as follows.

A pool of colostrum was prepared from 15 Swedish cows which calved in August-October 1999. The colostrum was collected 8–80 hours postpartum in 4 consecutive milkings. Cream was scimmed off from the pool of colostrum. Rennet was added to the colostrum at 32° C. and after 30 minutes the coagulum was ready for cutting. Some of the whey was then pasteurised (60° C., 45 minutes) and freeze-dried yielding a freeze-dried whey powder that will be referred to as whey powder. A membrane separation technique was used for the further separation of the whey. Microfiltration (0.8 μm) was carried out for reduction of bacteria and removal of fat and extraneous particles. Ultrafiltration (cut off at 100 kDa) was performed in order to concentrate whey proteins and was followed by diafiltration with the same membrane to remove lactose and salts. The concentrate was pasteurised (60° C., 45 minutes) and freeze-dried yielding a freeze-dried immuno-globulin concentrate that is referred to as Ig concentrate. To produce 1 g of whey powder it takes 17.0 g of whole colostrum and to produce 1 g of Ig concentrate it takes 44.5 g whole colostrum.

Fermented oatmeal soup is a commercially available probiotic product produced by Skånemejerier, Sweden. Oat flour (780 g) and water (4.2 l) are blended together and malted barley flour (32 g) is added to the mixture. Malted barley flour contains amylase, proteinases, and beta-glucanases and is added to prevent gelatinisation of starch upon heating. The mixture is heated to 95° C. and then cooled to 37° C. The obtained oatmeal soup is then fermented with Lactobacillus plantarum 299v at 38° C. for 18 hours. The final product contains $1\cdot10^9$ colony forming units per gram fermented oatmeal soup. ProViva is a fruit drink comprising 5% by weight of this fermented oatmeal soup.

The protein content of the whey powder and of the Ig concentrate was determined using a Kjeldahl method by Svenska Mejerilaboratoriet AB. Lund, Sweden. The analysis was performed according to the International Dairy Federation Standard 20A:1986.

The protein content of the whey powder was 36.9 g/100 g. The Ig concentrate had a protein content of 86.0 g/100 g.

The method used to determine the concentration of bovine IgG was radial immunodiffusion. This technique is frequently used in studies of bovine colostrum (see for instance Chao-Cheng Chen et al., 1998, supra). In this study the radial immuno-diffusion kit for bovine IgG was from The Binding Site Limited, Birmingham, UK. In this method antigen diffuses from a cylindrical well through an agarose gel containing an appropriate amount of monospecific antibody. Antigen-antibody complexes are formed, which under the right conditions will form a precipitating ring. The size of the ring will increase until equilibrium is reached between the formation and the breakdown of complexes. By measuring the diameter of the ring for a number of standards with known concentration a calibration curve can be constructed. The concentration of antigen in an unknown sample can then be determined by measuring the ring diameter of the sample and reading the calibration curve.

In all assays performed the measurements were carried out according to the manufacturer's instructions, using procedure two. Three calibrators (250, 1500, 2500 mg/l) were used to produce a linear calibration curve. The dilution factor was determined for every sample depending on the estimated amount of IgG, to give results within the calibrator range. Samples and calibrators were added to the wells in an amount of 5 µl. Samples were analysed in duplicate, whereas the calibration standards were applied as single samples. For each new plate within the same batch the high calibrator was run to ensure that all plates were performing correctly. A new calibration curve was construed for every new assay. Rings were allowed to develop to completion, for which the recommended minimum time was 72 h. The rings were measured using a magnifying glass and a vernier calliper. The method was used to determine the concentration of IgG in samples from week 0, 2 and 4 of cool storage.

Storage Stability of Bovine IgG at Low pH

First the stability of bovine IgG at low pH was examined. Whey powder or Ig concentrate was dissolved in different buffers and distilled water to a concentration of 2.25% by weight. The citrate-HCl-NaOH buffers had pH-values of 3.00, 3.50 and 4.00. Powder dissolved in the distilled water gave the pH value 6.40. Before dissolving the powders the buffers and distilled water were sterilised and cooled to 60° C. The powder was then added aseptically and the temperature held at 60° C. for 10 minutes to give a mild pasteurisation. Each solution was divided into five equal parts and aseptically added to 100 ml bottles for storage at 6–8° C. Every week, that is from week 0 to week 4, one bottle was removed from the refrigerator, frozen and stored at a temperature below −18° C. until analysed.

Figure 1:
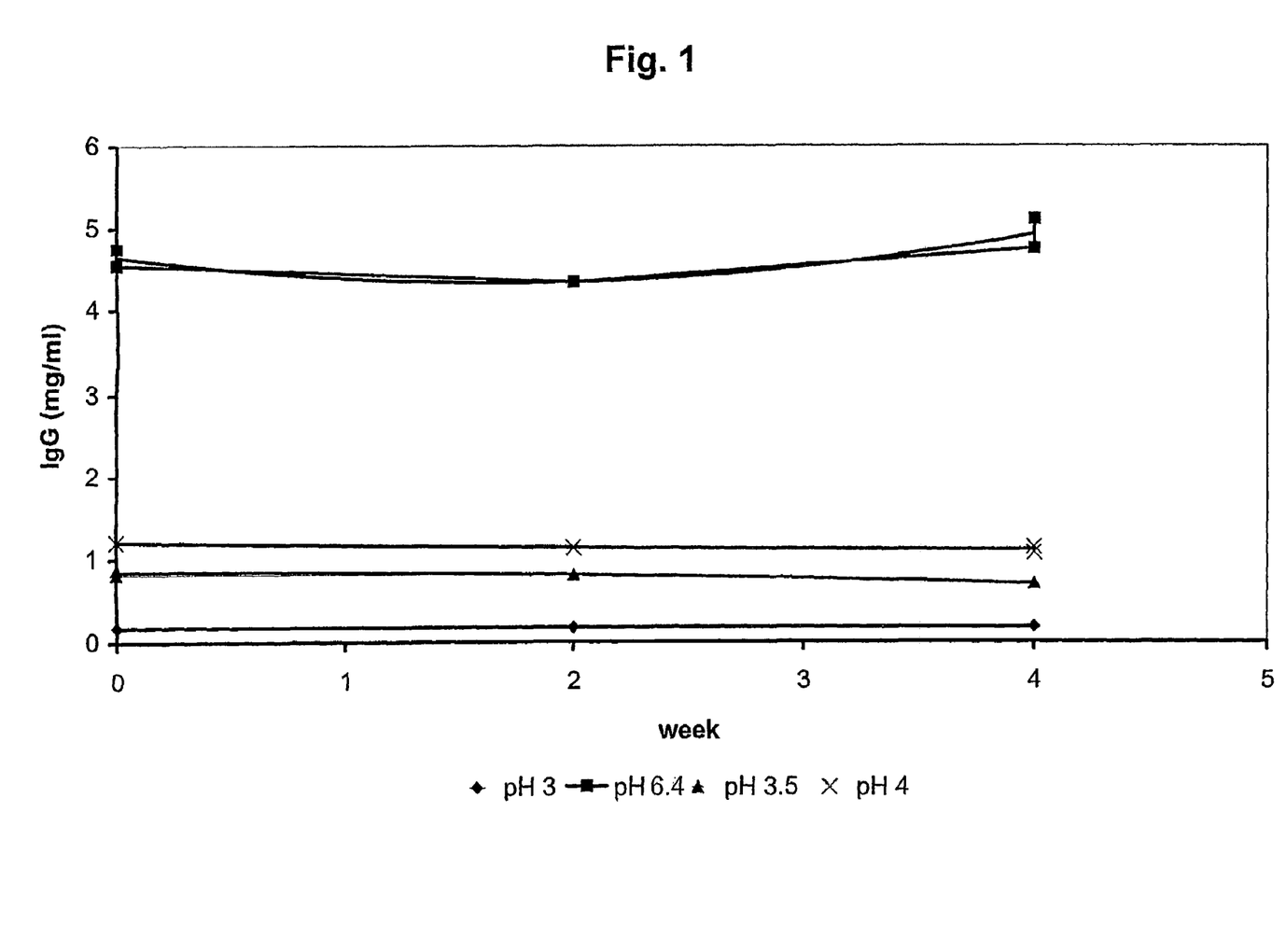
FIG. 1 shows the concentration of IgG in whey powder solutions at different pH during storage.
Figure 2:
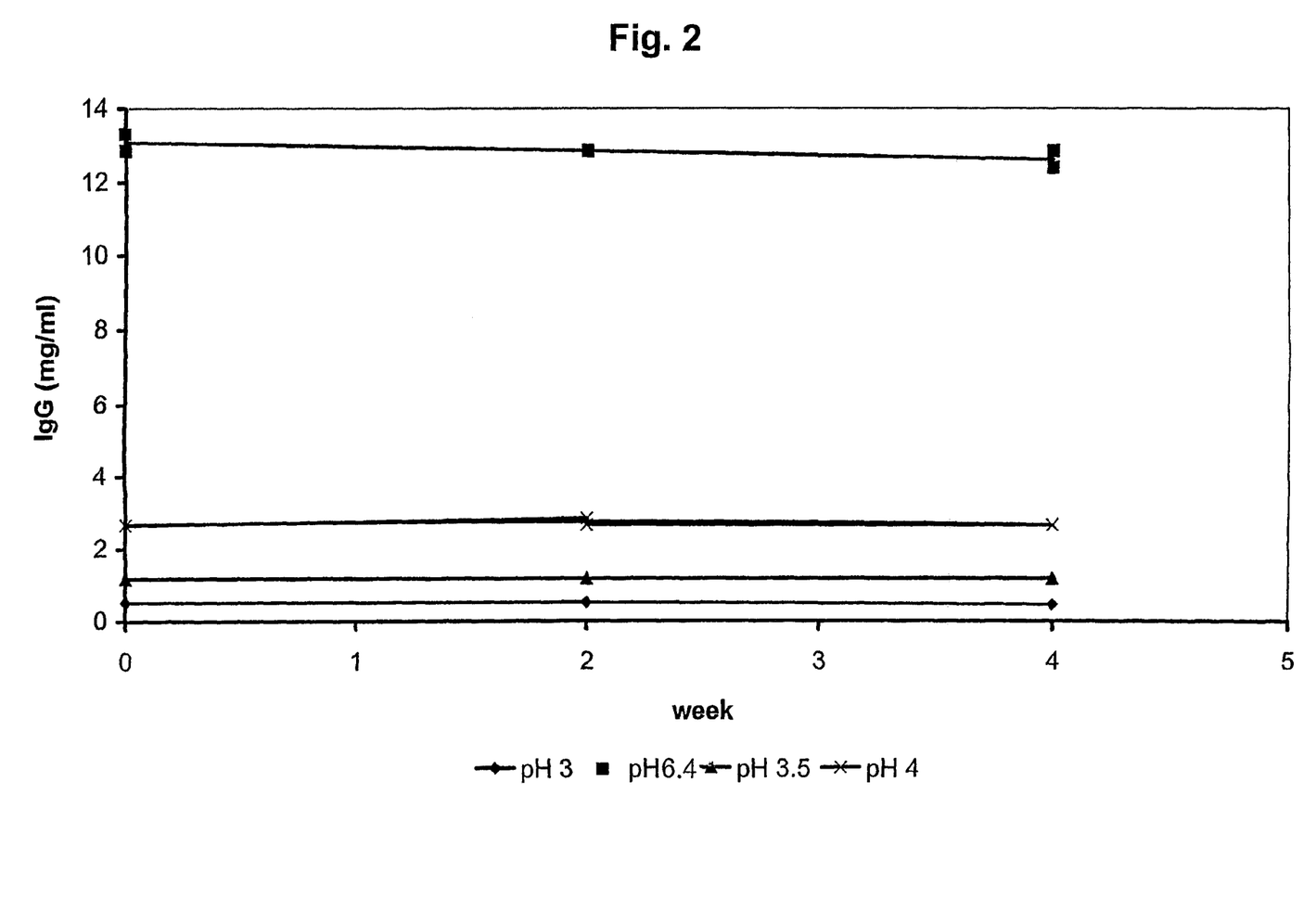
FIG. 2 shows the concentration of IgG in Ig concentrate at different pH during storage.

FIG. 1 shows the concentration of IgG in 2.25% whey powder solutions at different pH during storage. FIG. 2 shows the concentration of IgG in 2.25% solutions of Ig concentrate. The original concentration of IgG was the same in all buffers which indicates that the inactivation of IgG occurs within the period of time from preparing the sample until it is frozen after a few hours. At pH 6.4 bovine IgG is stable and the values can be used to calculate the IgG content of the colostrum protein powders.

The concentration of IgG in the IgG concentrate is 571∓13 mg/g and in the whey powder 206∓13 mg/g.

Figure 3:
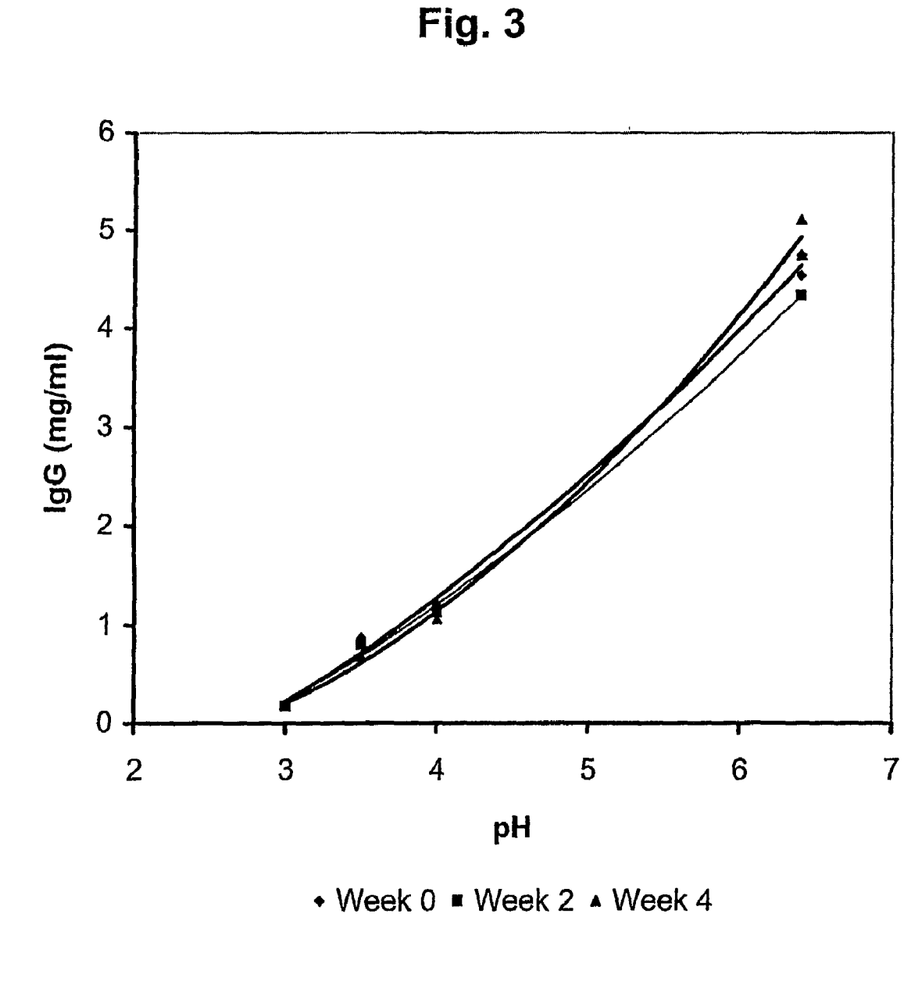
FIG. 3 shows the concentration of IgG in whey powder as a function of pH.
Figure 4:
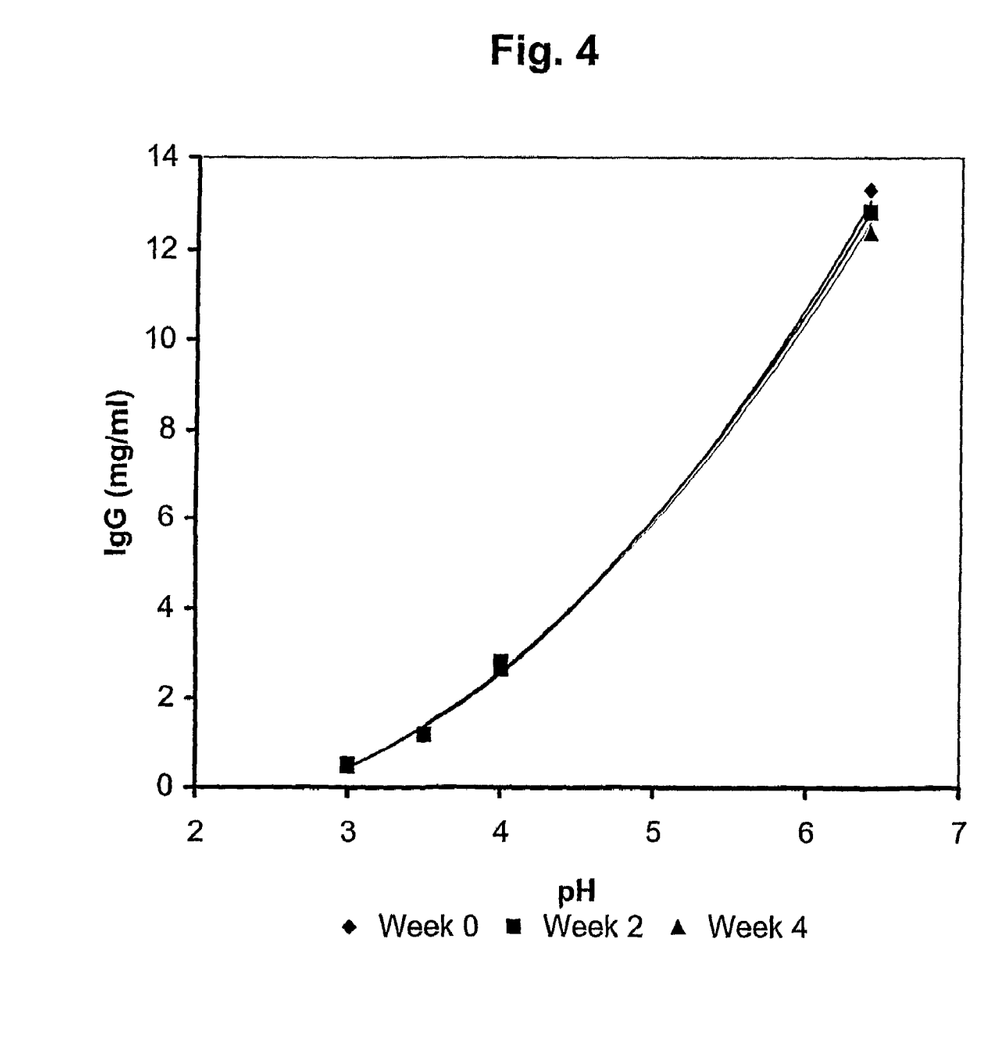
FIG. 4 shows the concentration of IgG in Ig concentrate as a function of pH.

The results also show that the pH value is of great importance for the stability of the bovine IgG, a finding that is illustrated more clearly in FIGS. 3 and 4. Here we can see that the stability of IgG drops quickly with decreasing pH. At pH 4 the concentration of IgG is only 21% of the original concentration in the Ig concentrate solutions, at pH 3.5 the concentration is 9% of the original and at pH 3 only 4%. The corresponding values for the whey powder are 25%, 17%, and 4%, respectively.

Storage Stability of Bovine IgG in Fermented Oatmeal Soup

In this test the interactions between the colostrum derived proteins and the bacteria were studied. Distilled water was sterilised and 2.25% by weight of whey powder or Ig concentrate was added at 60° C. The temperature was held for 10 minutes and the solutions were then cooled to about 30° C. Fermented oatmeal soup was then added to the bottles and to a reference bottle containing only sterile distilled water. The amount of fermented oatmeal soup was 5% by weight. The solutions were divided as above and stored at 6–8° C. Every week a bottle was removed form the refrigerator and analysed as to colony forming units and then frozen for later analysis of IgG.

There is no major change in concentration of bovine IgG in fermented oatmeal soup solution during cool storage for 4 weeks. Some inactivation has occurred during the first hours after preparation of the sample due to low pH. The concentration of IgG in the fermented oatmeal soup was 74% of the. original in the Ig concentrate samples and 92% in the whey powder samples. pH decreases with storage which is probably due to the production of lactate by the bacteria. Even though the pH decreases there is no decrease in IgG. At the end of the storage, that is after 4 weeks, the pH is below 4. As a comparison can be mentioned that the concentration of IgG in buffer solution at pH 4 was 25% of the original for the whey powder and 21% for the Ig concentrate.

Storage Stability of Bovine IgG in a Sports Drink

In this test the interactions between the colostrum derived proteins and the bacteria were studied in the presence of a complete fruit drink matrix. The ingredients of the drink matrix are as follows

| | |
|---|---|
| Dextrose | 60 g |
| Sucrose | 40 g |
| Fructose | 20 g |
| Fruit concentrate, Rauch NO 2790 | 15 g |
| Aroma, Quest lemon/lime | 1.5 g |
| Vitamins, minerals | 3.4 g |
| Fermented oatmeal soup, | 50 g |
| Water | 787.6 g |

Four different drinks were prepared. Three of them contained different proteins, namely Lacprodan® whey proteins (MD Foods, Viby, Denmark), whey powder, and Ig concentrate, respectively, in an amount of 22.5 g/l. Before the heat treatment all ingredients except the fermented oatmeal soup, vitamins and minerals were mixed. The drink without protein and the one containing Lacprodan® were heated in a water bath to 85° C. and held for 20 seconds before cooling to about 30° C. The drinks containing the colostrum derived proteins were given the same heat treatment but without the proteins. The proteins were instead added after cooling to 60° C., and the temperature was held for ten minutes before further cooling down to about 30° C. After cooling the fermented oatmeal soup was added in an amount of 5% by weight. The vitamins and minerals were also added at this stage. The drinks were divided into five parts and stored in bottles at 6–8° C. The same weekly procedure as for the samples in the tests above were carried out.

There was no major change in concentration of bovine IgG in the fruit drinks during cool storage for 4 weeks. Some inactivation did occur during the first hours after preparation of the samples due to low pH. The concentration of IgG in the fruit drink samples was 78% of the original in the Ig concentrate samples and 92% in the whey powder samples. The results indicate that the IgG in the whey powder solutions are more stable at low pH. pH decreases with storage which is probably due to the production of lactate by the bacteria. Even though the pH decreases there is no decrease in IgG. At the end of the storage, that is after 4 weeks, the pH is close to 3.5. As a comparison can be mentioned that the concentration of IgG in buffer solution at pH 3.5 was 17% of the original for the whey powder and 9% for the Ig concentrate.

The increased stability of the IgGs in fermented oatmeal soup solution, as well as in the fruit drink is of great interest.

It should be noticed that the amount of oats needed to stabilise IgG is surprisingly low, about 0.75 g per 100 g of solution.

Sensory Analysis of Different Sports Drinks

Five different fruit-drinks were tested in a blind sensory analysis. Seven subjects performed the test and graded the appearance, smell, consistency and taste of the drinks, as well as the overall impression. The scoring was on a five graded scale where 5 corresponded to "like a lot" and 1 to "dislike". The drinks were prepared from the fruit-drink matrix presented above to which had been added whey powder, Ig concentrate, or Lacprodan® in the amounts stated in Table 1 below. The protein content was the only thing differing between the fruit-drinks.

TABLE 1

Protein content of fruit-drinks

| Drink No. | 1 | 2 | 3 | 4 | 5 |
|---|---|---|---|---|---|
| Whey powder | — | — | — | — | 2.25% |
| Ig concentrate | 0.65% | 1.30% | 2.25% | — | — |
| Lacprodan ® | 1.60% | 0.95% | — | 2.25% | — |

The scorings from the sensory analysis are displayed as mean values for the seven subjects in the following Table 2.

TABLE 2

Scorings for different fruit-drinks

| Drink No. | 1 | 2 | 3 | 4 | 5 |
|---|---|---|---|---|---|
| Appearance | 4.29 | 3.57 | 2.29 | 4.86 | 2 |
| Smell | 3.57 | 3.57 | 3.43 | 4 | 2.43 |
| Consistency | 4.29 | 4 | 1.86 | 4.57 | 2.14 |
| Taste | 4 | 3.29 | 2 | 4.57 | 2.14 |
| Overall impression | 4.14 | 3.43 | 2.14 | 4.57 | 2.14 |

Drink number 4, which is a commercial sport recovery drink, had the best grades, followed by drinks number 1 and 2, which are also quite acceptable. The results show that a drink containing about 4–8 mg/ml of IgG is accepted from a sensory point of view.

Storage stability of bovine IgG in different components

Another assay was performed to determine which component or components that is responsible for the stabilising effect. In this experiment the fermented oatmeal soup was divided into its components, that is oatmeal soup, lactic acid and *Lactobacillus plantarum* 299v. Sample solutions were prepared by adding one of these components or a combination of components to buffer solutions at pH 3, 4 and 7. The components were added in the same amounts as in 5% fermented oatmeal soup. This procedure resulted in the following samples for each buffer: 1. reference with buffer only, 2. oatmeal soup, 3. lactic acid, 4. *Lactobacillus plantarum* 299v, 5. oatmeal soup+lactic acid, 6. fermented oatmeal soup. To the different solutions IgG concentrate was added in the amount of 2.25%. The samples were incubated at room temperature for 2 hours and then analysed for IgG. No heat treatment of the samples were used.

Figure 5:
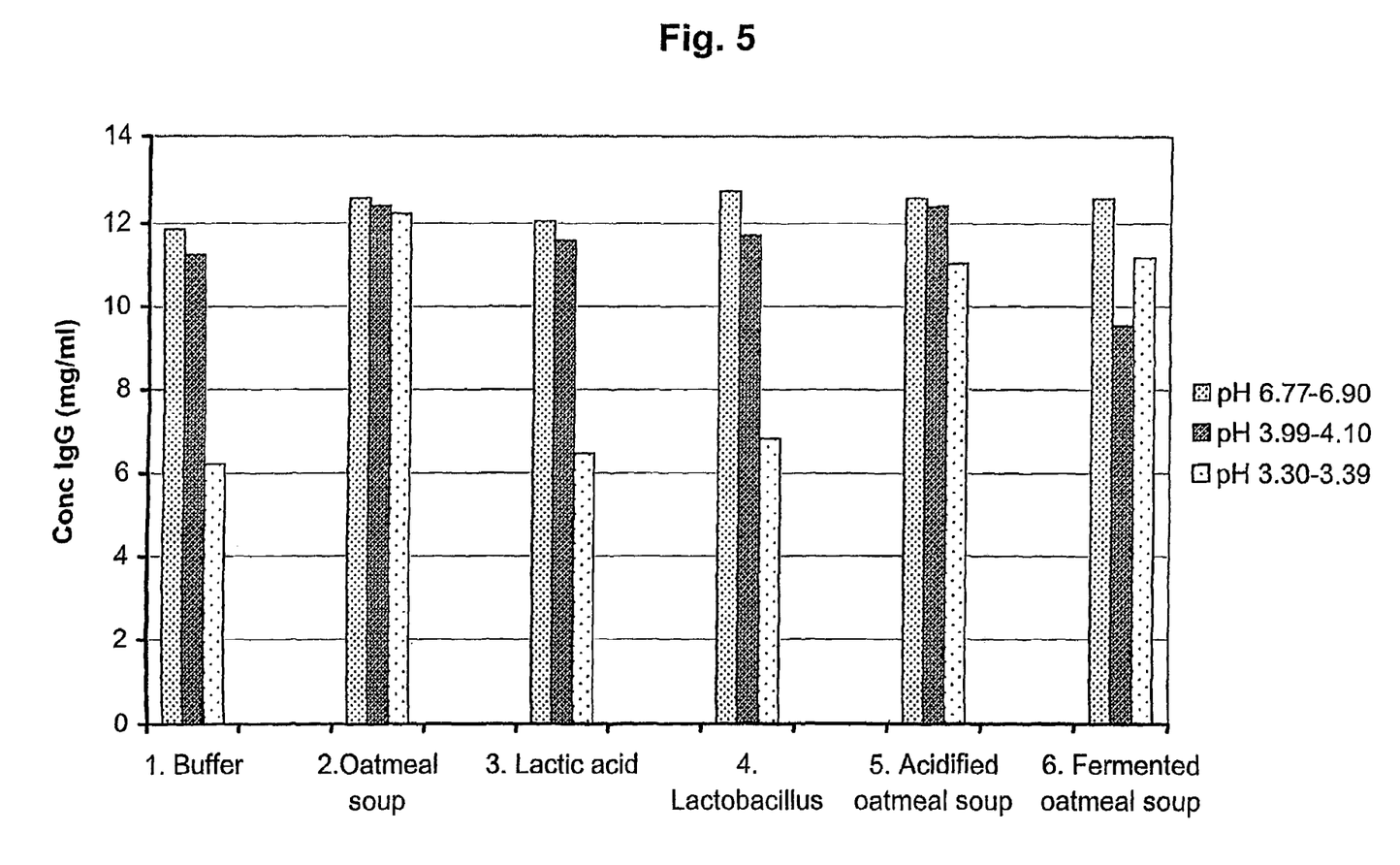
FIG. 5 shows the influence of different components on the concentration of IgG in a buffer containing 2.25% IgG concentrate at different pH.

The result of the analyses are shown in FIG. 5. The results show that oats is the component responsible for the stabilisation of IgG at low pH.

Storage Stability of Bovine IgG in a Fruit-Drink Matrix

The stabilising ability of a fruit drink on bovine IgG was tested by adding 2.25% IgG concentrate to the fruit-drink matrix described above, with and without fermented oatmeal soup. No heat treatment was used, and pH was about 3.0 in both drinks. The results are given in Table 3 below.

| | Amount of IgG, mg/ml |
|---|---|
| Drink with fermented oatmeal soup | 10.0 |
| Drink without fermented oatmeal soup | 9.5 |

The results show that the fruit-drink matrix alone, containing high amounts of sugar (i.e. mono-, di- and oligosaccharides), have a stabilising effect on IgG.

The invention claimed is:

1. Method of stabilizing immunoglobulins in a solution having a pH below 4, characterized in adding cereals or hydrolysed cereal products in an amount sufficient to prevent degradation.

2. Method according to claim 1, wherein the immunoglobulins are selected from the group consisting of IgG, IgA, 1gM and IgY.

3. Method according to claim 1, wherein the immunoglobulins are bovine IgGs.

4. Method according to claim 1, wherein oatmeal soup is added in an amount of from 2 up to 100% by weight of the solution.

5. Method according to claim 1, wherein oat flour is added in an amount of 0.3–15% by weight of the solution.

6. Method according to claim 1, wherein lipids from oats are added in an amount of 0.03–1.5% by weight of the solution.

7. Method according to claim 1, characterized in adding mono-, di- and/or oligosaccharides.

8. Method according to claim 1, characterized in adding a combination of cereals, sugars and fruit concentrate.

9. A health drink or sports drink comprising immunoglobulins in a solution having a pH of 2.7–3.8, characterized in containing cereals or hydrolysed cereal products in an amount sufficient to prevent degradation of the immunoglobulins.

10. A drink according to claim 9 containing an IgG concentrate in an amount of 0.5–50 mg IgG/ml.

11. A drink according to claim 9, wherein the immunoglobulins are bovine IgGs.

12. A drink according to claim 11, wherein the IgG concentrate is derived from bovine colostrum.

13. A drink according to claim 9, which in addition comprises a probiotic bacterium.

14. A drink according to claim 9, comprising sugars, fruit concentrate and fermented oatmeal soup.

15. A drink according to claim 13, wherein the probiotic bacterium is a strain of *Lactabacillus plantarum*.

16. A drink according to claim 9, which has a pH of 3.1–3.4.

17. A drink according to claim 9, wherein the immunoglobulins are stable for 4 weeks in storage at 6–8° C.

18. A drink according to claim 15, wherein the strain is *Lactobacillus plantarum* 299v, DSM 9843.

19. A drink according to claim 9, containing an IgG concentrate in an amount of 3–20 mg IgG/ml.

* * * * *